(12) United States Patent
Nasiatka et al.

(10) Patent No.: US 8,197,539 B2
(45) Date of Patent: Jun. 12, 2012

(54) INTRAOCULAR CAMERA FOR RETINAL PROSTHESES

(75) Inventors: Patrick J. Nasiatka, Westminster, CA (US); Michelle C. Hauer, Hawthorne, CA (US); Noelle R. B. Stiles, Orange, CA (US); Armand R. Tanguay, Jr., Yorba Linda, CA (US); Mark S. Humayun, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/744,714

(22) Filed: May 4, 2007

(65) Prior Publication Data

US 2008/0086206 A1    Apr. 10, 2008

Related U.S. Application Data

(60) Provisional application No. 60/746,588, filed on May 5, 2006.

(51) Int. Cl.
   *A61F 2/16* (2006.01)
(52) U.S. Cl. ............... 623/4.1; 623/6.63; 607/54
(58) Field of Classification Search ............ 623/4.1, 623/6.63; 607/54
   See application file for complete search history.

(56) References Cited

U.S. PATENT DOCUMENTS

| | | | | |
|---|---|---|---|---|
| 4,601,545 A | * | 7/1986 | Kern | 349/200 |
| 4,628,933 A | * | 12/1986 | Michelson | 607/53 |
| 4,642,112 A | * | 2/1987 | Freeman | 623/6.3 |
| 4,659,197 A | | 4/1987 | Weinblatt | |
| 4,799,931 A | * | 1/1989 | Lindstrom | 623/5.13 |
| 5,109,844 A | * | 5/1992 | de Juan et al. | 607/53 |
| 5,270,748 A | | 12/1993 | Katz | |
| 5,391,202 A | * | 2/1995 | Lipshitz et al. | 623/6.34 |
| 5,631,704 A | * | 5/1997 | Dickinson et al. | 348/308 |
| 5,653,751 A | * | 8/1997 | Samiy et al. | 623/6.63 |

(Continued)

FOREIGN PATENT DOCUMENTS

WO    2006015315 A2    2/2006

(Continued)

OTHER PUBLICATIONS

Nasiatka, P. et al. Intraocular Camera for Retinal Prosthesis. Poster presented at the 2005 Annual Meeting of the Association for Research in Vision and Ophthalmology, Ft. Lauderdale, Florida, May 5, 2005. (1 page).

(Continued)

*Primary Examiner* — Paul Prebilic
(74) *Attorney, Agent, or Firm* — McDermott Will & Emery LLP

(57) ABSTRACT

An intraocular camera for retinal prostheses may include an optical imaging system comprising a set of optical elements for forming an image of the external world on an image sensor array, wherein the optical elements and the image sensor array may be enclosed in an implantable biocompatible housing that may employ haptic elements for stabilization within the eye. The set of optical elements may be designed to have a short focal length and to provide adequate resolution images that can be transformed into a set of stimulation signals applied to a pixellated microstimulator array. Transmission of the signals from the intraocular camera to a microstimulator driver circuit may be accomplished either by a wired or wireless communication device. Power and control signals may be provided to the intraocular camera by a wired or wireless communication device, or optically by means of ambient illumination or an optical beam.

46 Claims, 4 Drawing Sheets

U.S. PATENT DOCUMENTS

| | | | | |
|---|---|---|---|---|
| 5,682,199 | A | * | 10/1997 | Lankford ................. 348/72 |
| 5,760,871 | A | * | 6/1998 | Kosoburd et al. ............. 623/6.3 |
| 5,861,940 | A | | 1/1999 | Robinson et al. |
| 5,868,664 | A | * | 2/1999 | Speier et al. ................ 600/112 |
| 5,935,155 | A | * | 8/1999 | Humayun et al. ............. 607/54 |
| 6,066,171 | A | * | 5/2000 | Lipshitz et al. ............. 623/6.18 |
| 6,458,157 | B1 | | 10/2002 | Suaning |
| 6,536,898 | B1 | * | 3/2003 | Cathey, Jr. ................ 351/160 R |
| 6,554,444 | B2 | | 4/2003 | Shimada et al. |
| 6,920,358 | B2 | | 7/2005 | Greenberg et al. |
| 7,001,427 | B2 | | 2/2006 | Aharoni et al. |
| 7,079,900 | B2 | | 7/2006 | Greenburg et al. |
| 7,103,416 | B2 | | 9/2006 | Ok et al. |
| 2002/0138009 | A1 | * | 9/2002 | Brockway et al. ............ 600/485 |
| 2003/0156257 | A1 | | 8/2003 | Levola |
| 2003/0158588 | A1 | | 8/2003 | Rizzo et al. |
| 2004/0030383 | A1 | * | 2/2004 | Havey et al. ................. 623/4.1 |
| 2004/0054407 | A1 | * | 3/2004 | Tashiro et al. ............. 623/6.22 |
| 2004/0102843 | A1 | * | 5/2004 | Yagi ............................ 623/4.1 |
| 2004/0117011 | A1 | * | 6/2004 | Aharoni et al. ............. 623/6.11 |
| 2004/0172099 | A1 | * | 9/2004 | Eckmiller et al. ............. 607/54 |
| 2005/0129755 | A1 | * | 6/2005 | Levy et al. .................... 424/451 |
| 2005/0209691 | A1 | * | 9/2005 | Aharoni et al. ............. 623/6.11 |
| 2005/0267329 | A1 | * | 12/2005 | Konstorum et al. ......... 600/112 |
| 2006/0069416 | A1 | * | 3/2006 | Nisch et al. .................... 607/54 |
| 2006/0238707 | A1 | | 10/2006 | Elvesjo et al. |
| 2006/0247734 | A1 | * | 11/2006 | Greenberg et al. ............. 607/54 |
| 2007/0191910 | A1 | * | 8/2007 | Ren ................................ 607/54 |

FOREIGN PATENT DOCUMENTS

WO         2007106145 A1       9/2007

OTHER PUBLICATIONS

Stroh, M. We See the Future Better Than 20/20. Popular Science, Jun. 2005. pp. 58-59.

Nasiatka, P. et al. Intraocular Camera Design for Retinal Prostheses. Paper presented to the 2005 Annual Meeting of the Optical Society of America, Tucson, Arizona, Oct. 2005. (1 page).

Amendment filed on Sep. 15, 2004 in response to Office Action mailed May 17, 2004 for U.S. Appl. No. 10/321,793, filed Dec. 17, 2002 entitled "Intraocular Implants."

European Patent Application No. 07794645.5, Amended Claim Set Submitted to the European Patent Office Jan. 27, 2009. European Regional Phase Application of WO 2007/130686 A2, entitled "Intraocular Camera for Retinal Prostheses," filed May 7, 2007 (International Application counterpart to U.S. Appl. No. 11/744,714).

European Patent Application No. 07794645.5, Extended European Search Report, dated Mar. 29, 2011, Regional Phase Application of WO 2007/130686 A2, entitled "Intraocular Camera for Retinal Prostheses," filed May 7, 2007 (International Application counterpart to U.S. Appl. No. 11/744,714).

Remarks On Information Disclosure Statement, filed May 12, 2011 for U.S. Appl. No. 11/744,714.

* cited by examiner

INTRAOCULAR CAMERA FOR RETINAL PROSTHESES

CROSS-REFERENCE TO RELATED APPLICATIONS

This application claims priority to U.S. Provisional Application Ser. No. 60/746,588 filed on May 5, 2006, entitled "Intraocular Camera for Retinal Prosthesis," the entire content of which is incorporated herein by reference.

STATEMENT REGARDING FEDERALLY SPONSORED RESEARCH

This invention was made with government support under Grant No. NSF EEC-0310723, awarded by the National Science Foundation. The government has certain rights in the invention.

BACKGROUND

1. Field

This application relates generally to prosthetic devices and methods for restoring sight to the blind.

2. Description of Related Art

Among the many causes of blindness, retinitis pigmentosa (RP) and age-related macular degeneration (AMD) are prevalent, causing catastrophic damage to the photoreceptor layer within the retina. Recent studies have demonstrated, however, that the inner layers of the retina remain for the most part intact even many years after the onset of the disease and the cessation of useful visual acuity. Furthermore, it has been shown that local electrical stimulation of the output ganglion cell layer leads to viable visual percepts, suggesting the possibility of developing retinal prostheses and restoring vision. Based on these findings, both epiretinal and subretinal microstimulator arrays have been developed to provide retinotopic stimulation. Two approaches have been used previously to supply images of the external world to the microstimulator array: (1) the incorporation of light sensitive elements within the microstimulator array itself, and (2) the use of an external camera, mounted for example on a pair of eyeglasses.

The incorporation of photosensitive elements within the microstimulator array itself has the apparent advantage of using the existing corneal lens and crystalline lens for the formation of the optical image. The incorporation of photosensitive elements within microstimulator arrays is described in A. Y. Chow, V. Y. Chow, M. T. Pardue, G. A. Peyman, C. Liang, J. I. Pearlman, and N. S. Peachey, "The Semiconductor-Based Microphotodiode Array Artificial Silicon Retina", IEEE International Conference on Systems, Man, and Cybernetics, 1999, 4, 12-15, 404-408, (1999) and F. Gekeler, H. Schwahn, A. Stett, K. Kohler, and E. Zrenner, "Subretinal Microphotodiodes to Replace Photoreceptor-Function: A Review of the Current State" Les Seminaires Ophtalmologiques d'IPSEN, 12, 77-95, (2001).

However, the implementation of such photosensitive elements within the microstimulator array has proven to be problematic for a number of reasons. The retina itself is a curved surface, and the optics of the eye are designed to focus onto this curved (Petzval) surface. Hence, implantation of a microstimulator array with photosensitive elements incorporated on a planar substrate, such as is typical of most semiconductor devices and very large scale integrated (VLSI) circuits, becomes increasingly difficult as the size of the microstimulator array increases. Second, the retinal tissue itself is fragile, and is easily damaged by the proximal implantation of devices with hard edges; again as is characteristic of most semiconductor devices and very large scale integrated (VLSI) circuits. Fabricating a microstimulator array with incorporated photosensitive elements on a pliable or curved substrate is problematic because most semiconductor materials capable of supporting photosensitive elements, and of also supporting necessary circuitry for biasing and gain, and neither pliable nor curved. Third, the incorporation of photosensitive elements without associated amplification is not capable of providing signals that are directly appropriate for localized electrical stimulation of the inner or outer layers of the retina. Fourth, the incorporation of photosensitive elements within the microstimulator array itself requires a tradeoff of space (area on the supporting substrate) between the photosensitive elements and any associated circuitry, on the one hand, and the stimulation electrodes and any associated circuitry and electrical connections (interconnection wiring, or metal traces) on the other hand. As microstimulator arrays are scaled up to higher and higher densities, the available space is increasingly required for the stimulation electrodes and interconnection wiring, leaving little if any space for localized photosensitive elements. Fifth, the incorporation of photosensitive elements (and any associated amplifiers, transformers, or signal conditioners) within the microstimulator array places an additional source of heat dissipation directly in contact with the thermally-sensitive retina itself, whether the microstimulator array is implanted subretinally or epiretinally. Sixth, the provision of electrical power for signal amplification at the surface of the retina is challenging, requiring an additional wired or wireless interconnection to the microstimulator array from the power source. Finally, the incorporation of photosensitive elements within the microstimulator array makes the implementation of post-image-acquisition but pre-stimulation image processing functions problematic, as either additional power consumptive circuitry must be added to the microstimulator array to perform these functions, or a wired or wireless interconnection must be provided to an ancillary device within which such processing is performed.

Additionally, the use of an external camera for capturing images of the external world would require implanted patients to employ (at times rapid) head motion to search the visual field or track moving objects, which can in turn lead to disorientation, dizziness, and nausea. Furthermore, the natural tendency of patients to foveate to the most visually interesting or important part of a scene would be to no avail with an externally-mounted camera coupled to the (internal) microstimulator array.

Miniature cameras have been developed for a wide range of applications, including surveillance, automated inspection, inspection in harsh environments, and certain biomedical applications. Such miniature cameras are not amenable to implantation within the human eye, as they are not designed specifically to work in conjunction with the biological corneal lens to comprise a two lens system that can form appropriate images of the external world on an image sensor array. In addition, they are too large to fit within the confines of the human eye, much less the confines of a supportive membrane such as the crystalline lens sac. The size of such cameras has been limited in large part by the difficulty of designing very short focal length lenses in the range of 1 to 3 mm with acceptable optical imaging performance. Miniature cameras developed to date have too high a mass to be supported within the human eye in general, and within the crystalline lens sac in particular, especially considering the needs for chronic implantation and rapid foveation. Such miniature cameras are also too power consumptive, which would lead to unacceptable temperature rises within the biological space surrounding an implanted intraocular camera.

SUMMARY

An intraocular camera for retinal prostheses may be used in place of an externally-mounted camera to provide capability for natural foveation, and may additionally provide an expanded depth of field that obviates the need for an additional accommodation mechanism. Furthermore, an advantage of the intraocular camera for retinal prostheses may be enhanced patient acceptability, as their appearance will be perceived as more typical of sighted individuals. In this context, exemplary embodiments of the intraocular "camera" may be described as intraocular video cameras, in that they may be capable of providing continuous (framed) video streams to the microstimulator array in real time or near real time. Provision for still image capture may be provided in such exemplary embodiments of intraocular cameras, in a manner that is either patient-controlled or physician-controlled, so that certain images within the patient's field of view may be studied in detail.

An intraocular camera for retinal prostheses may include a housing and an optical imaging system. The optical imaging system may include a set of optical elements, configured to be used in conjunction with the corneal lens or refracting surface, for forming images on an image sensor array. The optical elements and the image sensor array may be enclosed in a biocompatible and hermetic housing (housing enclosure) that can be chronically implanted within the human eye and that may employ haptic elements for stabilization. In some exemplary embodiments, either an optical window or one of the optical elements may be sealed to the housing enclosure, which thereby may comprise the optical window or an optical element (such as a lens, for example). One of a number of possible locations for surgical implantation may be within the crystalline lens sac, following a standard phacoemulsification procedure such as that employed in cataract removal surgery.

The set of optical elements may be designed to have a focal length of approximately 1 to 3 mm, and may include at least one of a refractive lens (e.g., a lens with spherical or aspherical surfaces), a gradient index (GRIN) lens, a pinhole lens, a diffractive lens, a hybrid refractive/diffractive lens, a diffractive optical element (DOE), a stratified volume diffractive optical element (SVDOE), and a stratified volume holographic optical element (SVHOE). The set of optical elements may be designed to provide adequate resolution images that can be transformed into a set of stimulation signals applied to a pixellated microstimulator array.

The set of optical elements may be antireflection coated (AR-coated) to eliminate spurious reflections and enhance image clarity in the presence of bright, localized light sources.

The set of optical elements incorporated in the intraocular camera for retinal prostheses may be used in conjunction with an external eyeglass or contact lens to correct for residual or acute misalignment error, placement error, optical image formation error, optical performance effects due to patient aging, or deformation of the corneal lens following surgical implantation of the intraocular camera for retinal prostheses.

Transmission of the analog or digital signals (or other signal formats that may be considered to be hybrids of analog and digital signals, such as ternary level encoding) from the intraocular camera to the microstimulator array through a microstimulator driver circuit may be accomplished either by a wired (e.g., a cable) or wireless communication device (e.g., electromagnetic or optical). An image data compression circuit can be included to reduce the required transmission bandwidth and dissipated power. Such transmission may either be direct, or through one or more external electronic devices, which may contain power transmission, control, image processing, signal conditioning, data transmission, data reception, and data storage circuits. In some embodiments, one or more of the external electronic devices may comprise the microstimulator driver circuit as well. The external electronic device may also contain one or more batteries.

One or more electronic circuits, of which one of several types are known to those skilled in the art as application specific integrated circuits (ASICs), may be incorporated in the intraocular camera to provide, for example, data transmission, data reception, image sensor array control, power control, microstimulator array driver, and environmental sensing functions, among others. These circuits may be integrated as one monolithic circuit incorporating the image sensor array, may be implemented as multiple electronic circuits or application specific integrated circuits, may be hybrid integrated with both discrete components and integrated circuits, or may be incorporated in one or more multichip modules or other advanced packaging technologies.

Power for the image sensor array and electronic circuits or application specific integrated circuits may be provided by one or more of a wired connection to a power source external to the eye, a wireless power source external to the eye, solar power, and optical power. In some exemplary embodiments, a power storage device may be incorporated within the intraocular camera for retinal prostheses, which may be rechargeable by means of any one or more of these power sources.

A desiccant or other moisture-absorbing substance may be included in the housing to provide for chronic gettering of any encapsulated moisture.

The intraocular camera may be configured to contain an optical window on the anterior (corneal-facing) surface of the biocompatible housing, such that the first optical imaging element is in contact with either gas or vacuum within the biocompatible housing and not with the aqueous humor.

The optical imaging system of the intraocular camera may include one or more diffractive optical elements that are designed to provide the focal power of a lens. The optical imaging system of the intraocular camera may also include one or more stratified volume diffractive optical elements (SVDOEs) or stratified volume holographic optical elements (SVHOEs) that are designed to provide the focal power of a lens. The SVDOE- or SVHOE-based optical imaging system may have several uses, such as providing separate focusing for an optical beam that is used to power the intraocular camera, or providing a higher resolution central vision region and a lower resolution peripheral vision region. The optical imaging system may comprise one or more refractive lens elements to produce the primary focal power of the imaging system, and one or more diffractive lenses, diffractive optical elements, or stratified volume diffractive (or holographic) optical elements that may be designed to correct for aberrations, or provide for simultaneous multiple uses as described above. In some embodiments, any one or more of these optical elements may be configured as a hybrid optical element, with one or more refractive surfaces, an axial or radial index gradient, and/or one or more diffractive surfaces, layers, or volume regions.

It is understood that other embodiments of intraocular cameras for retinal prostheses will become readily apparent to those skilled in the art from the following detailed description, wherein only exemplary embodiments of intraocular cameras are shown and described by way of illustration. As will be realized by those skilled in the art, such intraocular cameras are capable of other and different embodiments and its several details are capable of modification in various other respects, all without departing from the spirit and scope of the invention described herein. Accordingly, the drawings and detailed description are to be regarded as illustrative in nature and not as restrictive.

BRIEF DESCRIPTION OF THE DRAWINGS

Aspects of the present intraocular camera are illustrated by way of example, and not by way of limitation, in the accompanying drawings, wherein.

DETAILED DESCRIPTION OF ILLUSTRATIVE EMBODIMENTS

Figure 1:
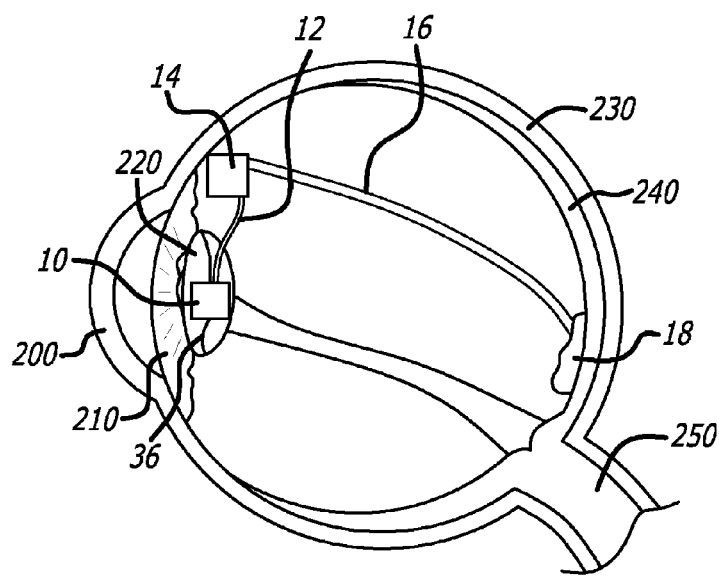
FIG. 1 is a schematic drawing illustrating the surgical implantation and placement of an exemplary intraocular camera for retinal prostheses within the crystalline lens sac.

The detailed description set forth below is intended as a description of exemplary embodiments of intraocular cameras for retinal prostheses and is not intended to represent the only embodiments in which such intraocular cameras and related image gathering methods can be practiced. The term "exemplary" used throughout this description means "serving as an example, instance, or illustration," and should not necessarily be construed as preferred or advantageous over other embodiments. The detailed description includes specific details for the purpose of providing a thorough understanding of the principles of operation and various embodiments of intraocular cameras for retinal prostheses. However, it will be apparent to those skilled in the art that the development and implementation of intraocular cameras for retinal prostheses may be practiced without these specific details. In some instances, well-known structures and devices are shown in block diagram form in order to avoid obscuring the concepts that illustrate intraocular camera form and function.

Exemplary embodiments of intraocular cameras for retinal prostheses teach the use of a surgically-implanted compact optical system for capturing images external to the eye. When connected to a microstimulator driver circuit as described herein, such intraocular cameras can be used to transfer these captured images in the form of electrical or chemical stimulation signals to the inner or outer layers of the retina by means of a pixellated microstimulator array. In the case of electrical stimulation signals, the transfer may be by means of a microstimulator electrode array, one of several possible implementations of a microstimulator array.

An exemplary intraocular camera for retinal prostheses comprises an optical imaging system, which further comprises a set of one or more optical elements (designed to be used in conjunction with the corneal lens or refracting surface) for forming an image of the external world on an image sensor array, with both the optical elements and the image sensor array enclosed in a biocompatible housing that is implanted within the human eye. One or more haptic elements included as part of or attached to the biocompatible housing may be employed for stabilization of the intraocular camera assembly. The optical imaging system and associated components may be enclosed in the biocompatible housing.

One of a number of possible locations for surgical implantation is within the crystalline lens sac, following a standard phacoemulsification procedure such as that employed in cataract removal surgery. This location has several advantages, including the support of the capsular bag (crystalline lens sac), if intact pre- or post-surgery; the availability of stable locations for haptic support within the crystalline lens sac or just external to it, without compromising the retinal surface; the separation of heat-dissipating elements (such as the image sensor array and any control circuitry, if included) from the thermally-sensitive retinal surface; and proximity to the thermalization capabilities of both the aqueous humor and vitreous humor.

The set of optical elements may be designed to have a short focal length (of approximately 1 to 3 mm), and may comprise at least one of a refractive lens (e.g., a lens with spherical or aspherical surfaces), a gradient index (GRIN) lens, a pinhole lens, a diffractive lens, a hybrid refractive/diffractive lens, a diffractive optical element (DOE), a stratified volume diffractive optical element (SVDOE), and a stratified volume holographic optical element (SVHOE), among other optical elements. In some exemplary embodiments, these elements may be used alone, and in others in various combinations to achieve a specific system focal length, magnification, aberration correction, and resolution at the focal plane (at or near the image sensor array). The optical element or elements that comprise the optical imaging system for the intraocular camera for retinal prostheses may be specifically designed to work in conjunction with (and as such may be considered to be corrected for) the dioptric power and aberrations of the biological corneal lens to produce optical images on the image sensor array. In some patients, the biological corneal lens may be replaced by a corneal transplant or an artificial cornea, with substantially similar optical properties to that of the biological cornea. It will be appreciated by those skilled in the art that the design of the optical element or elements that comprise the optical imaging system for the intraocular camera may be similar in all such cases, or may be sufficiently different that several variants of the basic optical system design will prove advantageous.

The set of optical elements may also be designed to provide adequate resolution images that can be transformed into a set of stimulation signals applied to a pixellated microstimulator array. The number of elements within the pixellated microstimulator array, as well as their size and spacing, may determine the minimum resolution required of the optical imaging system. Microstimulator arrays and corresponding systems known to those skilled in the art may be used with an exemplary embodiment of the intraocular camera; for example, systems and arrays are described in U.S. Pat. No. 6,533,798 to Greenberg, et al., the contents of which are incorporated herein by reference. In some embodiments, it may be advantageous for the reduction of aliasing to intentionally defocus the optical imaging system relative to the image sensor array by, for example, displacing the focal plane of the optical imaging system from the plane of the image sensor array in order to provide a pre-determined pre-pixellation blurring of the detected image.

The intraocular camera for retinal prostheses may also comprise one or more optical filters to enhance image contrast, or to delimit the optical spectrum that is imaged onto the image sensor array.

Provision may be made within the intraocular camera to allow for in situ adjustment of the position, rotation, or tilt of one or more optical elements or the image sensor array to allow for post-surgical implantation optimization of the image formation properties of the intraocular camera. In addition, provision may be made to allow for in situ adjustment of the focal length, optical transparency, or spectral transmission characteristics of one or more optical elements. For example, one or more of the optical elements or optical window that comprise the intraocular camera may be photochromic, so that illumination by bright light (as in the case of outdoor illumination in bright sunlight) causes gradual and reversible darkening of the optical element or optical window, thereby reducing its optical transparency. A variable aperture, for example an iris diaphragm, may also be provided to allow for in situ adjustment of the optical throughput, thereby effecting a variable f-number for the optical system of the intraocular camera. Such a photochromic optical element, photochromic optical window, or variable aperture may be used in conjunction with the image sensor array to provide extended dynamic range.

This degree of pre-determined blurring can also be implemented by relaxing the constraints of the optical imaging system with respect to Petzval surface curvature or other aberrations, provided that when taken in combination such aberrations provide appropriately uniform or non-uniform blurring of the image. One application of non-uniform blurring is the specification of sharper visual acuity in the central visual field, and of more diffuse visual acuity in the peripheral visual field, for cases in which the microstimulator array is designed to span a portion of both visual fields.

Based on extensive psychophysical experiments and analysis, in yet other exemplary embodiments it may be advantageous to blur the image after pixellation, and after application of image-derived electrical signals to the microstimulator array, insofar as it can produce blurring across pixels in the visual percepts of implanted patients. In this case, the elimination of artificial edges from the pixellation produced by a finite number of electrodes may be important for the brain to perceive naturally-occurring edges in the originally detected image. In addition, post-pixellation blurring may be advantageous for smoothing the effects of gridding within the microstimulator array, in which gaps between electrodes are included for electrical isolation, and may result in gaps in retinal excitation, particularly of the retinal ganglion cells. This post-pixellation blurring function typically cannot be implemented in the optical imaging system as in the case of pre-pixellation blurring as described above, nor can it typically be implemented in a post-image-sensor-array image processor. Instead, this post-pixellation blurring function may be implemented at the microstimulator array-retina interface by means of careful design of the individual electrodes within the array, such that current or electric field spreading is used to distribute a portion of the signal applied to one such electrode element to retinal cells in the proximity of neighboring electrode elements.

The combination of a very short focal length and a requirement for only adequate resolution matched to the low level of pixellation envisioned for microstimulator arrays (from 4×4 arrays as currently implanted in some ongoing surgical trials to 1,000×1,000 arrays in some projections) provides one of the benefits of exemplary embodiments of the present intraocular camera, namely, a very wide depth of field. In some instances, the depth of field may range from approximately 1 cm or less to infinity, providing a patient implanted with such an intraocular camera for retinal prostheses with the ability to magnify held or nearby objects far more than normally sighted individuals can. Such ability to magnify held objects may be limited by the resolution limitations of the microstimulator array. In this manner, a form of accommodation may be provided by the optical imaging system without the need for adaptive feedback control from the brain, nor for any moving or dynamically adjustable components.

The set of optical elements incorporated in the intraocular camera for retinal prostheses may be used in conjunction with an external eyeglass or contact lens to correct for residual or acute misalignment error, placement error, optical image formation error, optical performance effects due to patient aging, or deformation of the corneal lens following surgical implantation of the intraocular camera for retinal prostheses. The short focal length of the intraocular camera requires high dioptric power, and only relatively low dioptric power correction may be applied by the use of external eyeglass or contact lenses. Nonetheless, this feature of the invention may prove useful as a post-surgical correction procedure, or as an adaptive compensation feature for long term changes in the eye or optical imaging characteristics of the intraocular camera as used in conjunction with the corneal lens.

The set of optical elements, the optical window, and the image sensor array may be antireflection coated (AR-coated) to eliminate spurious reflections and enhance image clarity in the presence of bright, localized light sources. In addition, with one or more optical elements, the inclusion of antireflection coatings will increase optical throughput, and hence will enhance the low light sensitivity of the image sensor array and intraocular camera for retinal prostheses. The antireflection coatings may consist of single layer or multilayer thin film coatings designed to minimize reflections from the optical surface to which they are applied, over the spectral range envisioned for use (visible, near ultraviolet, near infrared, infrared, or combinations of these spectral ranges).

An image sensor or image sensor array may be employed to transform the optical image formed by the optical imaging system of the intraocular camera, which may be employed in conjunction with the corneal lens, to an electrical signal that represents the optical image. Various types of image sensor arrays can be used, including but not limited to charge-coupled devices (CCDs), complementary metal-oxide-semiconductor (CMOS) photosensitive arrays, active pixel sensor (APS) arrays, as well as many others known to those skilled in the art, including "cameras on a chip", biomimetic image sensors, and artificial retinas. In some embodiments, CMOS arrays in general, and APS arrays in particular, may be preferred over CCD sensor arrays, as they tend to operate at significantly lower power dissipation. The physical size of the envisioned image sensor array can be at the lower end of currently-available commercial image sensor arrays, as it should fit within the envisioned biocompatible housing. In an exemplary embodiment, the number of pixels incorporated in the image sensor array may exceed the number of microstimulator electrodes within the microstimulator array, based upon sampling considerations. In addition, the use of such a large number of pixels in the image sensor array may enable additional image processing operations to be performed prior to retinal stimulation, such as peripheral object location and motion detection. The pixel size of the image sensor array can be large enough to provide a good signal-to-noise ratio under conditions of low level illumination, such as moonlight or modest room lighting. Additionally, the dynamic range of the image sensor array, including either global or local gain control circuitry, may be wide enough to allow for operation in conditions of bright sunlight. In some embodiments, the output electrical signal may be either a linear or a nonlinear function of the incident irradiance within a given pixel of the image sensor array. For example the output electrical signal may be proportional to the logarithm of the incident irradiance, in order to provide for dynamic range compression and therefore expanded dynamic range. The format of the electrical signal may be either analog or digital, depending on the specific design of the image sensor array.

The spectral sensitivity of the image sensor array may include the visible spectrum (approximately 400 nm to 700 nm), a portion of the visible spectrum, the visible spectrum extended into the near ultraviolet (UV), the visible spectrum extended into the near infrared (IR), or the visible spectrum extended to both the near ultraviolet and the near infrared. Provision may be made to incorporate patient-selectable infrared image sensitivity, so that thermal sources may be more easily differentiated (e.g., a hot stove burner). This IR capability may be included in a separate image sensor array, or may be included in a hybrid image sensor array. Both color and monochrome image sensor arrays are to be considered a part of the invention. Color image sensor arrays may provide for enhanced chromatic object differentiation in post-processing prior to retinal stimulation, but may also increase the communications bandwidth required to transmit the output image (electronic) signal from the image sensor array to the microstimulator driver circuit. Monochrome image sensor arrays may provide a reduction in power consumption as well as a reduction in the communications bandwidth required to transmit the output image (electronic) signal from the image sensor array to the microstimulator driver circuit.

In order to reduce the mass of the image sensor array, as well as of any other very large scale integrated (VLSI) circuits included within the intraocular camera for retinal prostheses, the image sensor array and/or VLSI circuit substrates can be thinned below the usual thickness produced in commercial image sensor arrays and/or VLSI circuits by back-grinding, polishing, or a combination of these two techniques or other techniques known to those skilled in the art.

Transmission of the signals from the intraocular camera to a microstimulator driver circuit may be accomplished either by a wired (e.g., through a single-wire or multi-wire cable) or by a wireless communication device (e.g., electromagnetic or optical). In the wired communication case, an electrical via or feedthrough may be formed in the biocompatible housing to allow the wired connection to pass through. In this case, the microstimulator driver circuit may be located within the biocompatible housing of the intraocular camera, and the cable or other wired communication device may connect the microstimulator driver circuit to the microstimulator array. In an alternative set of embodiments, the microstimulator driver circuit may be located internal to the eye but separately from the intraocular camera housing, or even externally to the eye in a separate location. The choice of analog or digital transmission will be determined primarily, but not entirely, by the output signal format of the image sensor array.

In the wireless communication case, the microstimulator driver circuit may again be located internal to the eye but separately from the intraocular camera housing, or externally to the eye in a separate location. Both the wired and wireless communication devices (and their associated channels) may be unidirectional (for example, carrying the output image signal from the image sensor array to either the microstimulator driver circuit or a separate image processor module), or bidirectional (for example, carrying the output image signal from the image sensor array to either the microstimulator driver circuit or a separate image processor module, and in addition carrying camera control signals and power from external devices to the intraocular camera). The transmitting antenna (which may be in the form of a coil) may be incorporated within the biocompatible housing of the intraocular camera, or may be displaced from the biocompatible housing.

In one exemplary embodiment of the intraocular camera for retinal prostheses, the wireless communication may be implemented optically, for example by means of an optical source and optical source encoding and modulation circuit incorporated within the biocompatible housing, with one or more optical detectors incorporated in an external sensor location (outside the eye). In one such exemplary embodiment, one or more optical detectors may be incorporated in the rim of a pair of eyeglasses, and connected to an external electronic device either by a wired or wireless communication link. The optical source may be one or more of a solid state light emitting diode, a superluminescent light emitting diode, an edge-emitting semiconductor laser, and a vertical cavity surface emitting laser. The optical source may also comprise an internal or external optical emitter that may be used in conjunction with a reflective, transmissive, absorptive, or polarization element that is capable of modulation.

An image data compression circuit can be included to reduce the required transmission bandwidth and dissipated power of either the wired or wireless communication devices. This image data compression circuit may be included within the image sensor array in some exemplary embodiments in accordance with the teachings of the invention, and also may be implemented in a separate discrete or integrated circuit within the biocompatible housing of the intraocular camera. In some embodiments, the image data compression circuit may be programmable, with the programming accomplished either prior to surgical insertion, or after surgical insertion in an adaptive manner.

The electronic circuit for image data compression may be a part of one or more integrated circuits (ICs) that are included within the biocompatible housing of the intraocular camera. Additional functions that may be included in such an electronic or integrated circuit include power conditioning, power monitoring, closed loop power control, wired communications control, wireless communications control, data transmission, data reception, image sensor array control, image processing, and environmental sensing, among other functions. Examples of integrated circuits include application specific integrated circuits (ASICs), field programmable gate arrays (FPGAs), dynamic random access memory (DRAM), flash memory, static random access memory (SRAM), microprocessors, and controllers.

Power for the image sensor array and electronic or integrated circuits may be provided by one or more of a wired connection to a power source external to the eye, a wireless power source external to the eye, solar power, and optical power. In the case of a wired connection, an electrical via or feedthrough may be provided in the biocompatible housing of the intraocular camera, and a single or multiple wire cable routed through the sclera to an additional implanted device exterior to the eye that can supply the needed power, as currently implemented for provision of electrical power to the microstimulator array in several implementations that are based on an extraocular camera approach. In the case of a wireless connection, provision may be made for an intraocular coil to receive wireless power and data, located either internal or external to the biocompatible housing of the intraocular camera. In the case of an intraocular coil that is located external to the biocompatible housing, an electrical via or feedthrough may be provided in the biocompatible housing of the intraocular camera, and a single or multiple wire cable routed to the external coil. In the case of solar power, one or more solar cells may be included within the biocompatible housing of the intraocular camera, and illuminated by ambient illumination. In the case of optical power, one or more optical sources located external to the eye (for example, in a pair of eyeglasses) may illuminate one or more photosensitive elements located internal or external to the biocompatible housing of the intraocular camera. In the case of one or more photosensitive elements located exterior to the biocompatible housing of the intraocular camera, an electrical via or feedthrough may be provided in the biocompatible housing of the intraocular camera, and a single or multiple wire cable routed to one or more external photosensitive elements.

In several exemplary embodiments of the intraocular camera for retinal prostheses, a power regulation circuit may be included within the intraocular camera biocompatible housing to stabilize the power delivered to the intraocular camera image sensor array and electronic or integrated circuits. The power regulation circuit may be designed to accommodate for power fluctuations due to noise, the instantaneous power demand of the intraocular camera, or the effects of foveation on electromagnetic or optical power coupling. The power regulation circuit may also be designed to effect either open or closed loop control.

The biocompatible housing of the intraocular camera for retinal prostheses may be designed to contain the various intraocular camera elements, may be surgically implantable with relative ease through a moderate limbal or scleral incision (sclerotomy) among a number of other surgical techniques, and may be capable of conducting heat dissipated by the enclosed intraocular camera elements to the surrounding aqueous humor and vitreous humor without significant thermal buildup. The biocompatible housing may be configured in a number of appropriate shapes and sizes, of which one exemplary embodiment comprises a cylindrical enclosure, and another a rectangular enclosure. The housing enclosures may be configured as single-open-ended, double-open-ended, or variants thereof, with a lens, an optical element, or an optical window placed at or near the single open end in the first case, and at or near the anterior open end in the second case, with the other open end sealed with a plug. The advantage of a single-open-ended enclosure for this purpose is the elimination of one sealed joint, which may prove advantageous for chronic implantation.

The materials from which suitable biocompatible enclosures can be made include, but are not limited to, metals, polymers, ceramics, glasses, and plastics, as well as carbon fiber extrusions. Materials suitable for the biocompatible housing may be capable of hermetic sealing. The entire biocompatible housing may be hermetically sealed such that it is impervious to leakage under chronic implantation in the saline environment of the eye, thereby protecting the electronic circuits enclosed. In addition, the biocompatible housing may be formed in part from an external housing that is overcoated with a biocompatible coating, yielding enhanced hermeticity, biocompatibility, or thermal uniformity, among other possible functions. The biocompatible housing may be fully evacuated before sealing, or back-filled with inert gases at atmospheric or partial atmospheric pressure. Sealing with partial atmospheric pressure may be implemented, as it provides net positive pressure on the seal at either end of the enclosure under nearly all envisioned conditions, yet minimizes the pressure gradient from without to within the enclosure. Sealing with partial atmospheric pressure as opposed to full atmospheric pressure may also have the advantage of reducing the outward pressure exerted on the sealed end or ends of the biocompatible housing under conditions of travel to mountainous terrain or within private or commercial aviation vehicles.

A desiccant or other moisture-absorbing substance may be included in the biocompatible housing to provide for chronic gettering of any encapsulated or outgassed moisture. The desiccant may be included as a cylindrical ring that fits inside the biocompatible housing of the intraocular camera, as part of the biocompatible housing itself, or in a number of shapes and sizes within the biocompatible housing of the intraocular camera provided that it is placed such as not to impede the optical path of the optical imaging system.

An additional feature of the intraocular camera for retinal prostheses is the inclusion of one or more sensors within the biocompatible housing to monitor critical operational characteristics such as power dissipation, temperature, pressure, or humidity. Sensor outputs can be converted as necessary by means of an electronic or integrated circuit included within the biocompatible housing, and communicated to an external electronic device by either wired or wireless communication circuits.

Haptic elements may be mounted on the exterior of the biocompatible housing to allow for stable placement of the intraocular camera within (or with respect to) the eye, much as in the case of intraocular lenses (IOLs). In one exemplary embodiment of the intraocular camera, two haptic elements can be employed, one above and one below the biocompatible housing. This placement of the two haptic elements can oppose both the forces of gravity and any buoyancy force when the implanted patient is normally situated in an upright posture, yet may not be optimally placed when the implanted patient is reclining or inclined with respect to the surface of the earth. Other placements of the two haptic elements can be easily utilized, and may be employed depending on the condition of the implanted patient's eyes prior to surgery, as well as at the discretion of the surgeon, provided that such placement provides adequate stabilization of the intraocular camera in use. Provision may be made in each haptic element for suturing to help fixate each such element with respect to the eye itself. Similar suture provisions are routinely made for intraocular lenses.

In yet another exemplary embodiment of the intraocular camera, three haptic elements may be employed, displaced from each other by an angle of approximately 120 degrees. This configuration can result in increased stabilization of the intraocular camera with respect to both patient inclination and motion, though it may slightly increase the complexity of surgical insertion and suturing if required.

A further use of the haptic elements within the design of an intraocular camera for retinal prostheses is the dissipation of heat away from the biocompatible housing of the intraocular camera through conduction to the fluids within the eye, as well as potentially to the eye wall itself with its rich array of blood vessels.

Yet another use of the haptic elements within the design of an intraocular camera for retinal prostheses is the incorporation of an antenna or a portion of an antenna, comprising in turn a component of a wireless communication system as described further herein.

It will be easily appreciated by those skilled in the art that the haptic elements may be positioned along the optical axis of the biocompatible housing of the intraocular camera such that they are located at or near the center of mass of the intraocular camera for balance.

As exemplary embodiments of the intraocular camera can fit within a confined region of the eye, and in several exemplary embodiments to be supported in effect by a combination of the eye wall and the crystalline lens sac, exemplary embodiments of the intraocular camera may have a low mass. The mass of the human crystalline lens, which in several exemplary embodiments the intraocular camera is designed to replace, is estimated to be approximately 250 mg, and commonly used intraocular lenses are approximately 30 to 75 mg by way of comparison. As a consequence, the design of each component that comprises the intraocular camera may include low mass. The haptic elements used with exemplary embodiments of the intraocular camera can be designed specifically to support and stabilize the mass, net buoyancy, and dynamical characteristics of the intraocular camera.

Referring now to the figures, FIG. 1 depicts one exemplary embodiment of the intraocular camera for retinal prostheses, in which the intraocular camera 10 is surgically implanted within the crystalline lens sac 220 posterior to the iris 210, and is approximately centered along the optical axis of the eye (which is tilted relative to the physical axis of the eye) by one or more haptic support elements 36. An optical image of the external world is formed by the combined focal powers of the corneal lens 200 (or refracting interface) and the optical element or elements comprising the optical imaging system within the intraocular camera. The optical imaging system can be designed to account for not only the focal power of the corneal lens 200, but also its contributions to system aberrations, as the corneal lens 200 is normally used in a sighted individual in conjunction with the crystalline lens to form an image on the nearly spherical retinal focal plane 240 supported by the sclera 230 (which image is transmitted to the visual cortex through the optic nerve 250), and not on the flat focal plane of the image sensor array within the intraocular camera for retinal prostheses. Alternative placements of the intraocular camera can be implemented that place the intraocular camera only partially within the crystalline lens sac 220, or either anterior or posterior to the crystalline lens sac 220. Referring further to FIG. 1, the intraocular camera may be connected either by a wired (as shown) or wireless communication device 12 to the microstimulator driver circuit 14, shown in this exemplary embodiment as located exterior to the intraocular camera biocompatible housing as described above. The microstimulator driver circuit 14 is in turn connected by a micro-connector cable 16 to the microstimulator array 18 implanted either epiretinally (as shown) or subretinally at the posterior end of the eye. Examples of subretinal microstimulator arrays that may be used in optical imaging systems of the intraocular camera are described in the following articles, the contents of each of which are incorporated herein by reference: A. Y. Chow, V. Y. Chow, M. T. Pardue, G. A. Peyman, C. Liang, J. I. Pearlman, and N. S. Peachey, "The Semiconductor-Based Microphotodiode Array Artificial Silicon Retina", IEEE International Conference on Systems, Man, and Cybernetics, 1999, 4, 12-15, 404-408, (1999); J. Wyatt and J. Rizzo, "Ocular Implants for the Blind", IEEE Spectrum, 33 (5), 47-53, (1996); and F. Gekeler, H. Schwahn, A. Stett, K. Kohler, and E. Zrenner, "Subretinal Microphotodiodes to Replace Photoreceptor-Function: A Review of the Current State" Les Seminaires Ophtalmologiques d'IPSEN, 12, 77-95, (2001). Examples of epiretinal microstimulator arrays that may be used in optical imaging systems of the intraocular camera are described in the following articles, the contents of each of which are incorporated herein by reference: 1. M. Humayun, "Pattern Electrical Stimulation of the Human Retina", Vision Research, 39, 2569-2576, (1999); and M. Humayun, "Intraocular Retinal Prosthesis", Transactions of the American Opthalmological Society, 99, 277-300, (2001). An RF antenna is depicted for purposes of coupling wireless power into the microstimulator driver circuit, and also for unidirectional or bidirectional communication if desired between the microstimulator driver circuit and one or more external control devices. As the microconnector cable between the microstimulator driver circuit and the microstimulator array may provide either unidirectional or bidirectional communication as well, feedback from the microstimulator array can in this manner also be communicated to one or more external control devices. Electrical stimulation of the inner retinal layers (for epiretinal implantation) or outer retinal layers (for subretinal implantation) or both causes firing of output ganglion cells (approximately) beneath each microelectrode within the array, which in turn sends signals to the brain through the optic nerve that are interpreted as deriving from optical (light) stimulation, thus producing visual percepts.

Figure 2:
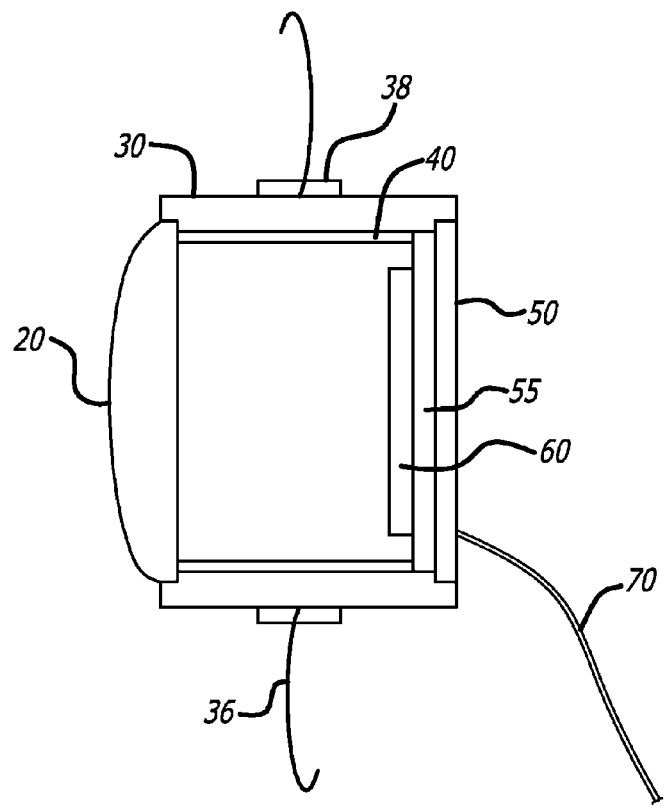
FIG. 2 provides a schematic diagram of an exemplary intraocular camera for retinal prostheses, comprising an optical imaging system (shown here by way of example as a lens), an image sensor array, an intraocular camera control and communications circuit, and a biocompatible double-ended (both ends open) housing enclosure.

FIG. 2 illustrates an exemplary embodiment of an intraocular camera for retinal prostheses. The intraocular camera comprises a lens 20 mounted in the anterior end of the biocompatible housing (facing the cornea); a biocompatible housing enclosure 30; two or more haptic elements 36 for stabilization of the intraocular camera within the eye that in turn may be attached directly to the biocompatible housing or to a haptic collar 38; an incorporated desiccant or moisture-absorbing compound 40; a posterior enclosure plug 50 that may comprise, incorporate, or support intraocular camera control and communication circuitry (mounted on a rigid or flexible printed circuit board, a multichip module, or a semiconductor substrate) 55; an image sensor array 60, and an output cable or wired communication device 70. If the biocompatible housing enclosure is single-ended (one end open), then a seal is provided between lens 20 and the biocompatible housing enclosure 30, and the posterior enclosure plug 50 may not be needed. If the biocompatible housing enclosure is double-ended (both ends open), then in addition to the seal provided between lens 20 and the biocompatible housing enclosure 30, a seal is provided between the posterior end plug 50 and the biocompatible housing enclosure 30.

In this exemplary embodiment, only a single refractive or gradient index lens element is used to comprise the optical imaging system, which contributes to the intraocular camera having low mass. Use of multiple refractive or gradient index lenses, in any combination, may be used to optimize the imaging characteristics of the optical imaging system (e.g., provide field-flattening, or minimize aberrations). The use of a single refractive or gradient index lens element may accompany a retinal prosthesis implementation with a low pixellation microstimulator array, such that the resolution required of the optical imaging system is reduced and more significant aberrations and more Petzval surface curvature may be tolerated.

If a single refractive lens 20 is employed, an exemplary embodiment comprises a low mass optical material with a relatively high index of refraction, such as is characteristic of several types of acrylic polymer lenses. Furthermore, the use of a single refractive lens element provides few degrees of freedom for aberration control, and as a consequence aspherical lenses may be used in several exemplary embodiments of the intraocular camera for retinal prostheses.

In order to provide for the shortest possible focal length of the system within given imaging constraints, the optical imaging system may operate at low f-number. For example, in exemplary embodiments employing a single refractive or gradient index lens, the f-numbers may be between approximately 0.7 and 1.2.

Figure 3:
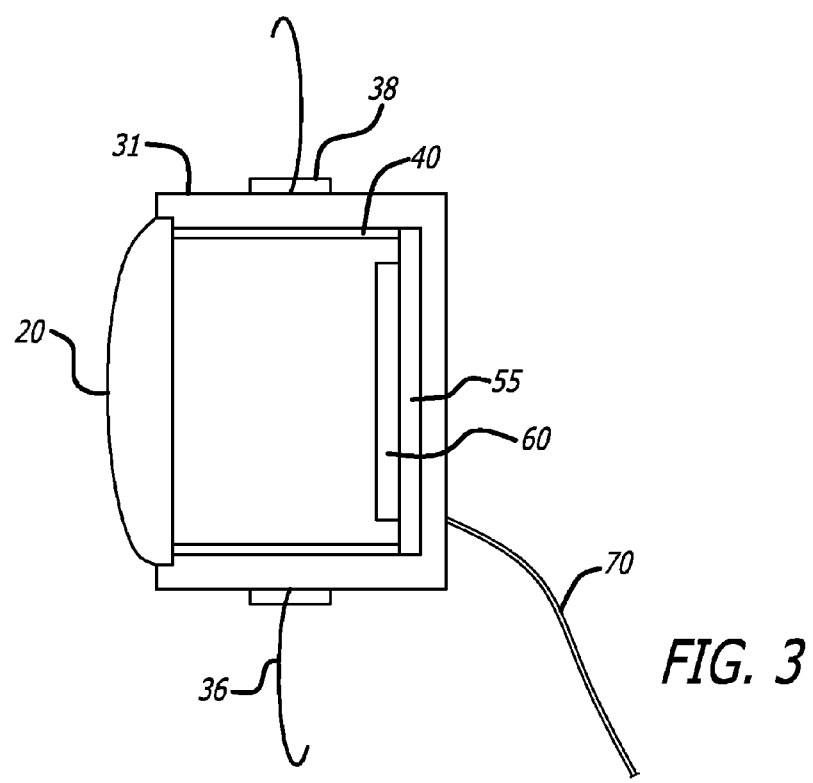
FIG. 3 provides a schematic diagram of an exemplary intraocular camera for retinal prostheses, comprising an optical imaging system (shown here by way of example as a single refractive lens), an image sensor array, and a biocompatible single-ended (anterior end open) housing enclosure.

Another exemplary embodiment is provided schematically in FIG. 3, which depicts an intraocular camera for retinal prostheses encapsulated in a single-ended biocompatible housing enclosure 31. In this exemplary embodiment, a seal may be located between lens 20 and biocompatible housing enclosure 31. This exemplary embodiment is differentiable on the basis of its housing configuration, and may contain any one of the optical imaging systems, image sensor arrays, desiccant materials, haptic support elements, and other components that comprise the intraocular camera for retinal prostheses.

Figure 4:
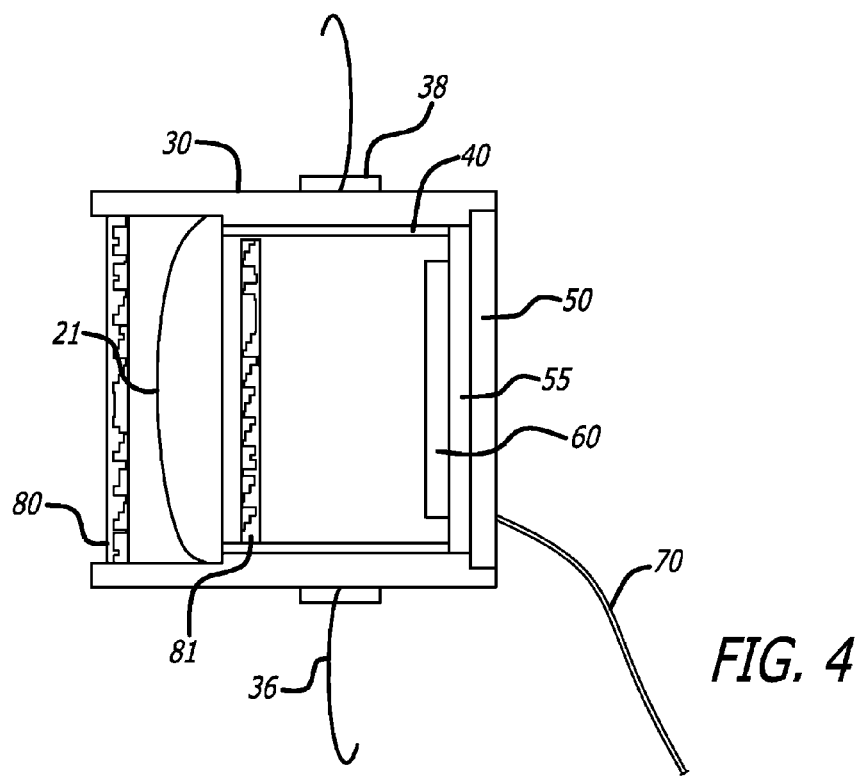
FIG. 4 provides a schematic diagram of an exemplary intraocular camera for retinal prostheses in which the optical imaging system comprises a refractive lens and two diffractive optical elements (DOE's).

Yet another exemplary embodiment of an intraocular camera for retinal prostheses is shown in FIG. 4, which depicts an optical imaging system comprising a single refractive lens and one or more diffractive optical elements (DOE's) 80 and 81. In the configuration shown, diffractive optical element 80 is placed anterior to the single refractive lens 21, and may be oriented so that the etched surface faces inward, thereby presenting a smooth outward surface to the interior fluids of the eye. The designs of the two diffractive optical elements 80 and 81 may vary among various embodiments, as might be expected by their relative positioning within the optical train. As a consequence, the design of the single refractive lens 21 may vary among these various embodiments as well, such that the single refractive lens 21 and diffractive optical elements 80 and 81 are co-designed. The entire optical imaging system can be designed to improve the imaging characteristics of the system while minimizing the mass of the optical elements used. As some focal power can be incorporated within the diffractive optical elements, in addition to their function as aberration-controlling elements, the curvature and focal power required of the single refractive lens 21 can be reduced, thereby improving ease of fabrication, potentially reducing cost, and also reducing the system mass if the offsetting masses of the diffractive optical elements are less than the mass reduction of the single refracting lens. Examples of DOE's and DOE design procedures that may be used in optical imaging systems of the intraocular camera are described in the following articles, the contents of each of which are incorporated herein by reference: J. R. Fienup, "Iterative Method Applied to Image Reconstruction and to Computer Generated Holograms," Optical Engineering, 19, 297-305 (1980); Victor A. Soifer, Methods for Computer Design of Diffractive Optical Elements, John Wiley and Sons, Inc., New York, (2002); and Donald C. O'Shea, Thomas J. Suleski, Alan D. Kathman, and Dennis W. Prather, Diffractive Optics: Design, Fabrication, and Test, SPIE Press, Bellingham, Wash., (2003).

Figure 5:
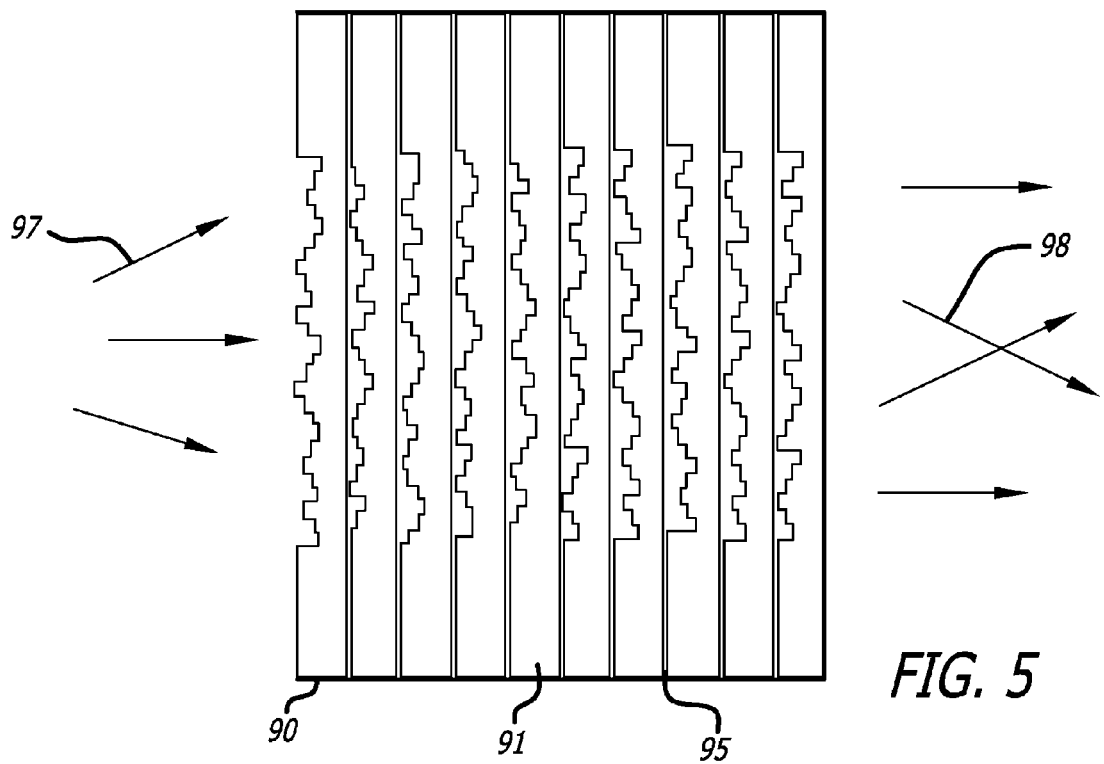
FIG. 5 illustrates a stratified volume diffractive optical element (SVDOE), comprising precisely-aligned multiple layers of planar diffractive optical elements.

An optical element that may be advantageous to the design of several exemplary embodiments of intraocular cameras for retinal prostheses is a stratified volume diffractive optical element (SVDOE) 90, as shown schematically in FIG. 5, in which a set of optical input beams 97 is transformed by the stratified volume diffractive optical element 90 to produce a set of optical output beams 98. Stratified volume diffractive optical elements 90 comprise a set of planar diffractive optical elements 91 that are co-designed to implement volume rather than planar diffraction characteristics. The implementation of volume diffraction characteristics allows for the multiplexing of several optical functions within a single optical device, such as the provision of focusing power, the separation of an infrared optical beam designed to provide power to the intraocular camera, and the provision for peripheral motion detection without direct peripheral imaging. Stratified volume diffractive optical elements or stratified volume holographic optical elements may be designed with one or more of these characteristics among other useful optical functions. Examples of SVDOEs, SVHOEs, and SVDOE and SVHOE design procedures that may be used in optical imaging systems of the intraocular camera are described in the following articles, the contents of each of which are incorporated herein by reference: Richard V. Johnson and Armand R. Tanguay, Jr., "Stratified Volume Holographic Optical Elements", Optics Letters, 13 (3), 189-191, (1998); Gregory P. Nordin, Richard V. Johnson, and Armand R. Tanguay, Jr., "Diffraction Properties of Stratified Volume Holographic Optical Elements", Journal of the Optical Society of America A, 9 (12), 2206-2217, (1992); Diane M. Chambers and Gregory P. Nordin, "Stratified Volume Diffractive Optical Elements as High-Efficiency Gratings", Journal of the Optical Society of America A, 16, 1184-1193, (1999); Diane M. Chambers, "Stratified Volume Diffractive Optical Elements," Ph.D. Thesis, University of Alabama-Huntsville, Huntsville, Ala., (2000); Diane M. Chambers, Gregory P. Nordin, and Seunghyun Kim, "Fabrication and Performance of a Three-Layer Stratified Volume Diffractive Optical Element High-Efficiency Grating", Optics Express, 11 (1), 27-38, (2003); P. Nasiatka, "Design, Fabrication, and Integration of a 3-D Hybrid Electronic/Photonic Smart Camera", Ph.D. Thesis, University of Southern California, Los Angeles, Calif., (2003); and Stefan Borgsmuller, Steffen Noehte, Christoph Dietrich, Tobias Kresse, and Reinhard Manner, "Computer-Generated Stratified Diffractive Optical Elements", Applied Optics, 42 (26), 5274-5283, (2003). Antireflection coatings 95 can be provided on both sides of the planar diffractive optical elements that comprise the stratified volume diffractive optical element 90 in order to minimize the often deleterious effects of multiple reflections on designed performance.

Figure 6:
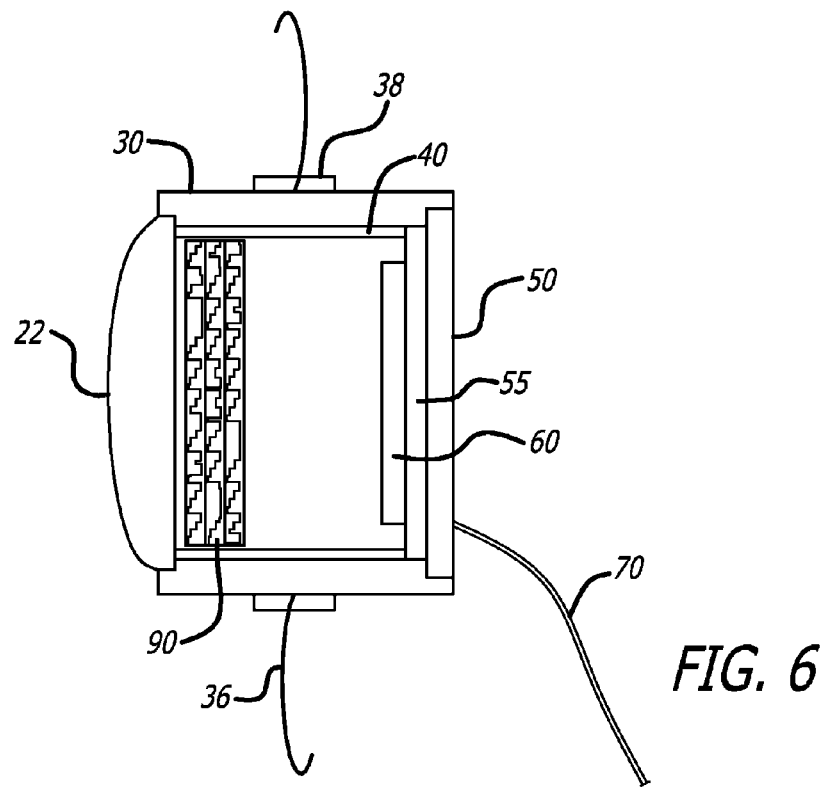
FIG. 6 provides a schematic diagram of an exemplary intraocular camera for retinal prostheses in which the optical imaging system comprises a refractive lens and a stratified volume diffractive optical element (SVDOE).

The utilization of a stratified volume diffractive optical element within an intraocular camera for retinal prostheses is depicted schematically in FIG. 6, wherein the stratified volume diffractive optical element 90 is placed following a single refractive lens 22. As before, the single refractive lens 22 is designed in conjunction with the stratified volume diffractive optical element 90, and hence in most cases differs in design from single refractive lenses 21 and 20, discussed previously. Similarly, stratified volume diffractive optical element 90 can be designed in conjunction with single refractive lens 22 to produce the desired combination of optical imaging system characteristics. Alternative placements of the single refractive lens 22 and stratified volume diffractive optical element 90 may be implemented. For example, the stratified volume diffractive optical element 90 can precede single refractive lens 22 in the optical train, forming the most anterior component of the intraocular camera for retinal prostheses. In this case, the etched surfaces of the stratified volume diffractive optical element could be reversed, such that a smooth window is presented to the interior fluids of the eye.

Figure 7:
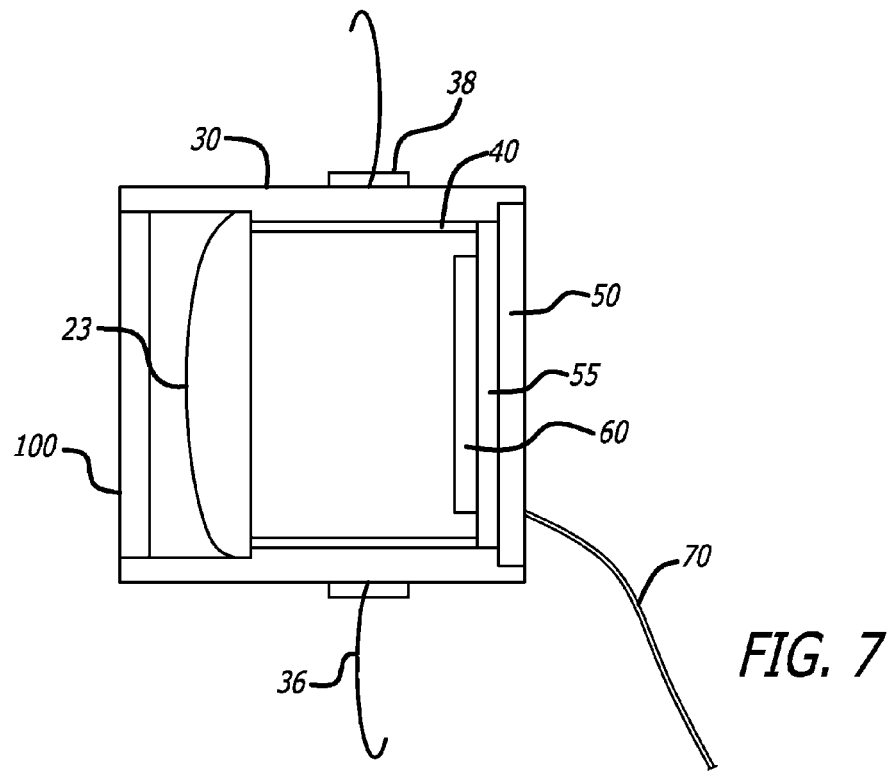
FIG. 7 provides a schematic diagram of an exemplary intraocular camera for retinal prostheses in which an optical window is incorporated on the anterior side of the biocompatible housing, facing the corneal lens.

Another exemplary embodiment of an intraocular camera for retinal prostheses is provided in FIG. 7, which depicts the inclusion of an exterior flat (shown) or curved optical window 100 at the anterior end of the biocompatible housing enclosure. The incorporation of optical window 100 may increase the index of refraction difference at the interface between the anterior-most surface of single refractive lens 23 and its surroundings, as the inclusion of the window displaces the aqueous humor from the anterior-most surface and replaces it instead with the gaseous or vacuum media internal to the biocompatible housing of the intraocular camera. This in turn may allow the single refractive lens 23 to have significantly less curvature on the anterior-most surface, thereby improving its aberration performance and decreasing its mass for a given constituent material. Various embodiments of the intraocular camera could be modified to include such an optical window.

Figure 8:
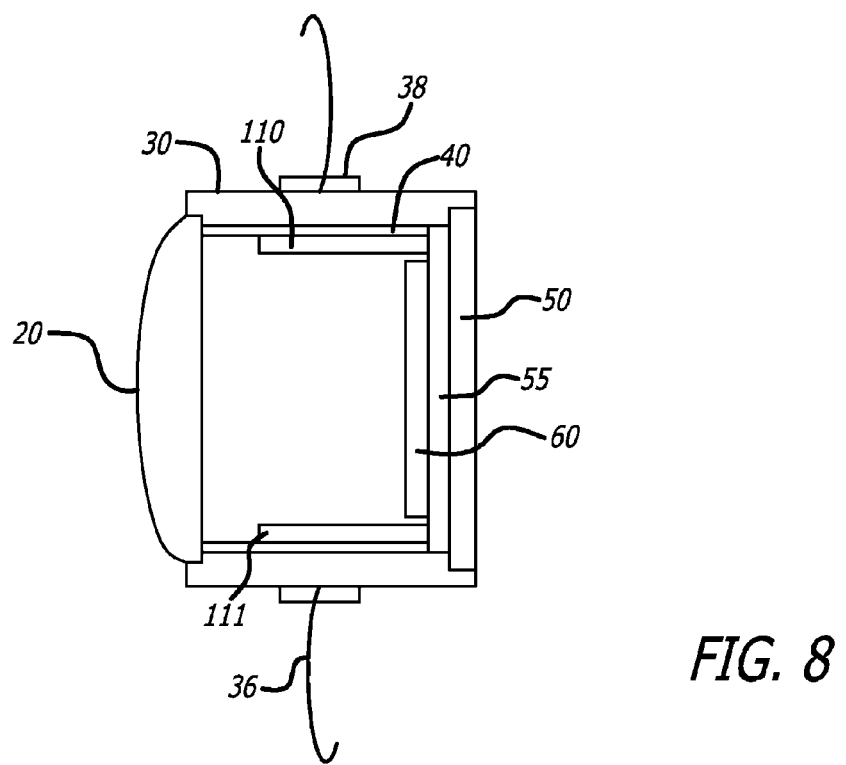
FIG. 8 provides a schematic diagram of an exemplary intraocular camera for retinal prostheses in which one or more application-specific integrated circuits (ASICs) are used for control of the image sensor array, for image data compression, for wired transmission, for wireless transmission, or for power conditioning.

Other exemplary embodiments of the intraocular camera may further include additional circuit elements such as application-specific integrated circuits (ASICs) or other discrete components (such as a quartz crystal oscillator to provide a clock signal) to perform various functions. One such exemplary embodiment is shown in FIG. 8, in which an intraocular camera for retinal prostheses based on a single refractive lens (by way of example) is depicted, incorporating additional circuit elements 110 and 111, mounted within the biocompatible housing enclosure such that they do not restrict the optical path of the optical imaging system, and connected to the image sensor array, its control and communications circuitry, other discrete components, or each other as dictated by the overall system design in each case.

Examples of such additional circuit elements include, but are not limited to, wired communication control circuits, wireless communication control circuits, power reception and conditioning circuits, image sensor array control circuits, image sensor array buffer memory, image processing function implementation circuits (for the implementation, for example, of image compression, image pixellation, signal averaging, noise reduction, dynamic range compression, lateral brightness adaptation, chromatic adaptation, global gain control, local gain control, adaptive gain control, and other image processing functions known to those skilled in the art), and environmental sensors and sensor amplifiers (such as power dissipation, temperature, pressure, and humidity).

In yet another exemplary embodiment of an intraocular camera for retinal prostheses, the corneal lens and crystalline lens may be left intact in the case of phakic patients, or the crystalline lens replaced with an intraocular lens as in the case of pseudophakic patients, with the image sensor array displaced to a position in the eye proximal to (but not in direct contact with) the retina. In this case, the technique of flip chip bonding can be gainfully employed for coupling of the image sensor array to an associated microstimulator driver circuit, and then to the microstimulator array that is either epiretinally or subretinally implanted. In this case, the biocompatible housing is not employed as described above, but instead is virtually included in the form of a hermetic coating on the surfaces of the image sensor array, microstimulator driver circuit, and microstimulator array (as necessary for chronic implantation).

The various elements that comprise this exemplary embodiment of an intraocular camera for retinal prostheses may be interconnected by a single wire carrying a multiplexed communication channel, by a multiple wire cable, or by attachment to a flexible cable (known to those skilled in the art as "chip-on-flex" packaging. This configuration provides both parallel interconnections and light weight.

In an exemplary embodiment, the circuit elements may be thinned by back-grinding, polishing, or a combination of the two techniques, as described earlier in the case of image sensor arrays.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of intraocular cameras for retinal prostheses. Thus, such intraocular cameras are not intended to be limited to the embodiments shown herein, but are to be accorded the widest scope consistent with the principles and novel features disclosed herein.

The invention claimed is:

1. An intraocular camera system, comprising:
    (a) at least one optical element configured to form an optical image;
    (b) an image sensor array configured to receive the optical image and convert the optical image to an electronic signal;
    (c) a biocompatible, hermetic housing enclosure configured to be implanted within a patient's eye and to contain the at least one optical element and the image sensor array;
    (d) a microstimulator driver circuit configured to receive data corresponding to the electronic signal; and
    (e) a microstimulator array configured to stimulate the patient's retina based on the electronic signal.

2. The intraocular camera system of claim 1, wherein the intraocular camera system further comprises a circuit configured to communicate with at least one external electronic device.

3. The intraocular camera system of claim 1, further comprising an image data compression circuit located within or external to the housing enclosure.

4. The intraocular camera system of claim 1, wherein the at least one optical element provides specified blurring of the image received by the image sensor array.

5. The intraocular camera system of claim 1, wherein the position of the at least one optical element relative to the position of the image sensor array provides specified blurring of the image received by the image sensor array.

6. The intraocular camera system of claim 1, wherein the housing enclosure further comprises an optical window, and wherein the at least one optical element is displaced from the optical window.

7. The intraocular camera system of claim 1, wherein the housing enclosure is configured to be placed within the crystalline lens sac of a patient's eye.

8. The intraocular camera system of claim 1, wherein the housing enclosure is configured to be placed either anterior or posterior to the crystalline lens sac of a patient's eye.

9. The intraocular camera system of claim 1, wherein the housing enclosure is configured to be placed partially anterior and/or posterior to the crystalline lens sac of a patient's eye.

10. The intraocular camera system of claim 1, wherein at least one optical surface of the at least one optical element and/or the image sensor array is coated with an antireflection coating.

11. The intraocular camera system of claim 6, wherein at least one optical surface of the at least one optical element and/or the optical window is coated with an antireflection coating.

12. The intraocular camera system of claim 1, wherein the intraocular camera system further comprises a circuit configured to receive wired power from at least one external electronic device.

13. The intraocular camera system of claim 1, wherein the intraocular camera system further comprises a circuit configured to receive externally generated wireless power transmission from at least one external electronic device.

14. The intraocular camera system of claim 1, wherein the intraocular camera system further comprises an optical detector and a power conditioning circuit.

15. The intraocular camera system of claim 13, wherein the circuit and/or the at least one external electronic device are configured to dynamically control the externally generated wireless power transmission.

16. The intraocular camera system of claim 1, further comprising a plurality of optical elements configured to form the optical image.

17. The intraocular camera system of claim 16, wherein the plurality of optical elements comprises at least one refractive lens and at least one stratified volume diffractive optical element.

18. The intraocular camera system of claim 16, wherein at least one optical surface of at least one optical element of the plurality of optical elements and/or the image sensor array is coated with an antireflection coating.

19. The intraocular camera system of claim 2, further comprising an element configured to receive control signals from the at least one external electronic device.

20. The intraocular camera system of claim 1, wherein the at least one optical element is adjustable.

21. The intraocular camera system of claim 1, further comprising a circuit configured to control the image sensor array.

22. The intraocular camera system of claim 1, wherein the at least one optical element is selected from the group consisting of: a refractive lens, a gradient index lens, a diffractive lens, a hybrid refractive/diffractive lens, a diffractive optical element, a stratified volume diffractive optical element, and a stratified volume holographic optical element.

23. The intraocular camera system of claim 1, further comprising an inert gas sealed within the housing at a full or partial atmospheric pressure.

24. The intraocular camera system of claim 1, wherein the microstimulator array is configured to be surgically implanted within the patient's eye epiretinally.

25. The intraocular camera system of claim 1, wherein the microstimulator array is configured to be surgically implanted within the patient's eye subretinally.

26. The intraocular camera system of claim 1, wherein the at least one optical element is configured to correct for the dioptric power and aberrations of a biological corneal lens and to form the optical image received by the image sensor array.

27. The intraocular camera system of claim 1, wherein the at least one optical element is configured to correct for the dioptric power and aberrations of an artificial corneal lens and to form the optical image received by the image sensor array.

28. The intraocular camera system of claim 1, further comprising at least one haptic element configured to stabilize the housing enclosure within the patient's eye.

29. The intraocular camera system of claim 1, further comprising either an eyeglass and/or a contact lens external to the patient's eye, configured to correct for any one of housing enclosure misalignment errors, housing enclosure placement errors, optical image formation errors, optical performance changes resulting from patient aging, or deformations of a patient's corneal lens.

30. The intraocular camera system of claim 1, wherein the image sensor array comprises a plurality of pixels, and wherein the number of pixels in the image sensor array is either equal to or greater than the number of microstimulator elements within the microstimulator array.

31. The intraocular camera system of claim 1, wherein the image sensor array, microstimulator driver circuit, and microstimulator array are further configured to generate data corresponding to a video stream, and wherein the microstimulator driver circuit and microstimulator array are configured to stimulate the retina based on the video stream in real time or near real time.

32. The intraocular camera system of claim 1, wherein the image sensor array, microstimulator driver circuit, and microstimulator array are further configured to generate data corresponding to still images in a manner controlled by the patient and/or a physician, and wherein the microstimulator driver circuit and microstimulator array are configured to stimulate the retina based on the still images in real time or near real time.

33. The intraocular camera system of claim 1, wherein the at least one optical element consists of a single optical element.

34. The intraocular camera system of claim 33, wherein the single optical element is a refractive lens.

35. The intraocular camera system of claim 33, wherein the single optical element is a gradient index lens.

36. The intraocular camera system of claim 33, wherein the single optical element is a diffractive lens.

37. The intraocular camera system of claim 33, wherein the single optical element is a hybrid refractive/diffractive lens.

38. The intraocular camera system of claim 33, wherein the single optical element is a diffractive optical element.

39. The intraocular camera system of claim 33, wherein the single optical element is a stratified volume diffractive optical element.

40. The intraocular camera system of claim 33, wherein the single optical element is a stratified volume holographic optical element.

41. The intraocular camera system of claim 1, in which the at least one optical element is configured to have a short focal length of approximately 1 to 3 mm.

42. The intraocular camera system of claim 22, in which the plurality of optical elements are configured to have a short focal length of approximately 1 to 3 mm.

43. The intraocular camera system of claim 1, in which the intraocular camera system is configured to have a wide depth of field, ranging from approximately 1 cm or less to infinity.

44. The intraocular camera system of claim 22, wherein at least one surface of the at least one optical element is either spherical or aspherical.

45. The intraocular camera system of claim 16, wherein the plurality of optical elements comprises a combination of at least one refractive lens and at least one diffractive optical element.

46. The intraocular camera system of claim 22, further comprising a plurality of optical elements configured to form the optical image.

* * * * *